(12) United States Patent
McKenna et al.

(10) Patent No.: US 7,314,489 B2
(45) Date of Patent: Jan. 1, 2008

(54) METHOD AND APPARATUS TO FACILITATE NUTRITIONAL MALABSORPTION

(75) Inventors: Robert Hugh McKenna, Cincinnati, OH (US); Jean Michael Beaupre, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 410 days.

(21) Appl. No.: 10/644,571

(22) Filed: Aug. 20, 2003

(65) Prior Publication Data

US 2005/0043817 A1 Feb. 24, 2005

(51) Int. Cl.
*A61F 2/36* (2006.01)
*A61M 5/32* (2006.01)

(52) U.S. Cl. .................... 623/23.65; 604/523

(58) Field of Classification Search .... 623/23.65–23.7; 604/8, 9, 264, 523, 220, 500; 606/108, 191, 606/198

See application file for complete search history.

(56) References Cited

U.S. PATENT DOCUMENTS

| | | | |
|---|---|---|---|
| 2,127,903 A | 8/1938 | Bowen | |
| 4,134,405 A | 1/1979 | Smit | |
| 4,315,509 A | 2/1982 | Smit | |
| 4,501,264 A | 2/1985 | Rockey | |
| 4,641,653 A | 2/1987 | Rockey | |
| 4,719,916 A | 1/1988 | Ravo | |
| 4,878,905 A | 11/1989 | Blass | |
| 5,306,300 A | 4/1994 | Berry | |
| 5,540,713 A | 7/1996 | Schnepp-Pesch et al. | |
| 5,820,584 A | 10/1998 | Crabb | |
| 6,132,471 A | 10/2000 | Johlin, Jr. | |
| 6,267,988 B1 | 7/2001 | Meyer | |
| 6,302,917 B1 | 10/2001 | Dua et al. | |
| 6,576,009 B2 * | 6/2003 | Ryan et al. ................ 623/1.35 |
| 6,675,809 B2 | 1/2004 | Stack et al. | |
| 2002/0032487 A1 | 3/2002 | Dua et al. | |
| 2003/0040804 A1 | 2/2003 | Stack et al. | |
| 2003/0109931 A1 | 6/2003 | Geitz | |

(Continued)

FOREIGN PATENT DOCUMENTS

EP 1 057 457 A1 12/2000

(Continued)

OTHER PUBLICATIONS

Weight Loss Surgery: Gastric Bypass Operations, WebMD Health, www.webmd.com.

(Continued)

*Primary Examiner*—Alvin J. Stewart
(74) *Attorney, Agent, or Firm*—Frost Brown Todd, LLC (57) ABSTRACT

A method and apparatus to facilitate nutritional malabsorption by diverting digestive secretions, such as bile or pancreatic secretions. A tube is positioned substantially within the small intestine. The tube comprises a proximal end which when deployed is operative to receive digestive secretions, a distal end which when deployed is operative to discharge the digestive secretions into the alimentary tract, and a tube wall having an inner surface and an outer surface, the tube wall inner surface defining passage extending between the proximal and distal ends. When deployed the passage is operative to transfer the digestive secretions from the proximal end to the distal end thereby reducing digestive contact between the digestive secretions and food in the small intestine.

17 Claims, 5 Drawing Sheets

U.S. PATENT DOCUMENTS

| | | |
|---|---|---|
| 2004/0039452 A1 | 2/2004 | Bessler |
| 2004/0092892 A1 | 5/2004 | Kagan et al. |
| 2004/0143342 A1 | 7/2004 | Stack et al. |
| 2004/0219186 A1 | 11/2004 | Ayres |
| 2004/0220682 A1 | 11/2004 | Levine et al. |
| 2004/0249362 A1 | 12/2004 | Levine et al. |

FOREIGN PATENT DOCUMENTS

| | | |
|---|---|---|
| WO | WO03/017882 | 3/2003 |
| WO | WO-03094785 A1 | 11/2003 |
| WO | WO2004/087233 | 10/2004 |

OTHER PUBLICATIONS

Arthur C. Guyton, M.D. and John E. Hall, Ph.D., Textbook of Medical Physiology, pp. 746-751, W.B. Saunders Company, Philadelphia, PA.

Kees Huibregtse and Vinod Dhir, Biliary Stenting, pp. 199-212.

Richard A. Kozarek, Bridging Intestinal Narrowing with Prostheses, pp. 39-58.

EP Search Report Dated Mar. 6, 2006, for EP Patent App. No. 04255027.7.

EP Search Report Dated Oct. 26, 2006, for EP Patent App. No. 04255027.7.

* cited by examiner

METHOD AND APPARATUS TO FACILITATE NUTRITIONAL MALABSORPTION

BACKGROUND

It is generally recognized that the mouth is the beginning of the digestive tract, also known as the alimentary tract. Digestion starts as soon as you take the first bite of a meal. Chewing breaks the food into pieces that are more easily digested, while saliva mixes with food to begin the process of breaking it down into a form the body can absorb and use. The throat, also called the pharynx, is the next destination for food. From here, food travels to the esophagus or swallowing tube.

The esophagus is a muscular tube extending from the pharynx to the stomach. By means of a series of contractions, called peristalsis, the esophagus delivers food to the stomach. Just before the connection to the stomach there is a zone of high pressure, called the lower esophageal sphincter, which functions something like a valve to keep food from passing backwards into the esophagus. The stomach is a sac-like organ with strong muscular walls. In addition to holding the food, it is also a mixer and grinder. The stomach secretes acid and powerful enzymes that continue the process of breaking the food down. When food leaves the stomach, it is the consistency of a liquid or paste. From there the food moves to the small intestine.

The small intestine is a long tube loosely coiled in the abdomen and is made up of three segments (the duodenum, jejunum, and ileum). The small intestine continues the process of breaking down food by using digestive secretions comprising enzymes released by the pancreas and bile from the liver. Peristalsis is also at work in the small intestine, moving food through and mixing it up with digestive secretions. The duodenum is largely responsible for continuing the process of breaking down food, with the jejunum and ileum being mainly responsible for the absorption of nutrients into the bloodstream.

Three organs help the stomach and small intestine digest food: the pancreas, liver, and gallbladder. Among other functions, the pancreas secretes enzymes into the small intestine. These enzymes break down protein, fat, and carbohydrate from the food we eat. The liver has many functions, two of which are to make and secrete bile, and to cleanse and purify the blood coming from the small intestine containing the nutrients just absorbed. Bile is a compound that aids in the digestion of fat and eliminates waste products from the blood. The gallbladder is a reservoir that sits just under the liver and stores bile. Bile travels from the liver to the gallbladder through a channel called the cystic duct. During a meal, the gallbladder contracts sending bile to the small intestine. Once introduced into the small intestine, the bile and pancreatic secretions aid in the digestion of food.

Once the nutrients have been absorbed and the leftover liquid has passed through the small intestine, the remainder is passed to the large intestine, or colon. The colon is a long muscular tube that connects the small intestine to the rectum. It is made up of the ascending colon, the transverse colon, the descending colon, and the sigmoid colon that connects to the rectum. Stool, or waste left over from the digestive process, is passed through the colon by means of peristalsis, first in a liquid state and ultimately in solid form. As stool passes through the colon, the rest of the water is removed. Stool is stored in the sigmoid colon until a mass movement empties it into the rectum. The stool itself is mostly food debris and bacteria. These bacteria perform several useful functions, such as synthesizing various vitamins, processing waste products and food particles, and protecting against harmful bacteria. When the descending colon becomes full of stool, or feces, it empties its contents into the rectum to begin the process of elimination.

The rectum is a short chamber that connects the colon to the anus. It is the rectum's job to receive stool from the colon and to hold the stool until evacuation happens. When anything (gas or stool) comes into the rectum, sensors send a message to the brain. The brain then decides if the rectal contents can be released or not. If they can, the sphincters relax and the rectum contracts, expelling its contents. If the contents cannot be expelled, the sphincters contract and the rectum accommodates, so that the sensation temporarily goes away.

The anus is the last part of the digestive tract. It consists of the pelvic floor muscles and the two anal sphincters (internal and external muscles). The lining of the upper anus is specialized to detect rectal contents, indicating whether the contents are liquid, gas, or solid. The pelvic floor muscle creates an angle between the rectum and the anus that stops stool from coming out when it is not supposed to. The anal sphincters provide fine control of stool. The internal sphincter is always tight, except when stool enters the rectum.

BRIEF SUMMARY OF THE INVENTION

One example of the invention is an apparatus for diverting digestive secretions, such as bile or pancreatic secretions. The apparatus comprises a tube which when deployed is positioned substantially within the small intestine. The tube comprises a proximal end which when deployed is operative to receive digestive secretions, a distal end which when deployed is operative to discharge the digestive secretions into the alimentary tract, and a tube wall having an inner surface and an outer surface, the tube wall inner surface defining passage extending between the proximal and distal ends. When deployed the passage is operative to transfer the digestive secretions from the proximal end to the distal end and the tube wall is operative to separate the digestive secretions from food in the small intestine.

Another example of the invention is an apparatus to facilitate nutritional malabsorption by diverting bile and pancreatic secretions. A tube comprises a proximal end, a distal end, a tube wall having an inner surface and an outer surface, and a passage extending between the proximal end and distal end and being defined by the inner surface of the wall. A stent is connected to the proximal end of the tube and being dimensioned for engaging an anatomical lumen (such as the hepatopancreatic ampulla, bile duct, pancreatic duct, and/or duodenum) through which digestive secretions flow. When deployed in a patient the stent is positioned in the anatomical lumen, a substantial portion of the tube is positioned in the small intestine, and the bile and pancreatic secretions of the patient enter the proximal end, flow through the passage and discharge from the distal end into the small intestine or large intestine thereby reducing digestive contact between the bile and pancreatic secretions and food in the small intestine.

Yet another example of the invention is a method to treat obesity by diverting digestive secretions to facilitate malabsorption. A tube is placed in the small intestine of a patient, the tube comprising a proximal end, a distal end, a tube wall having an inner surface and an outer surface, a passage extending between the proximal end and distal end and being defined by the inner surface of the wall, and a stent connected to the proximal end. The stent is attached in or near the major duodenal papilla such that the proximal end of the tube receives bile and pancreatic secretions. The distal end of the tube is in the small intestine of a patient in a location distal to the major duodenal papilla. Digestive contact is prevented between the bile and pancreatic secretions and food in the small intestine by passing bile and pancreatic secretions through the tube passage. The bile and pancreatic secretions are discharged from the distal end of the tube into the small intestine.

The foregoing brief description of examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

BRIEF DESCRIPTION OF DRAWINGS

While the specification concludes with claims which particularly point out and distinctly claim the invention, it is believed the present invention will be better understood from the following description taken in conjunction with the accompanying drawings, in which like reference numerals identify the same elements and in which:

DETAILED DESCRIPTION

Figure 1:
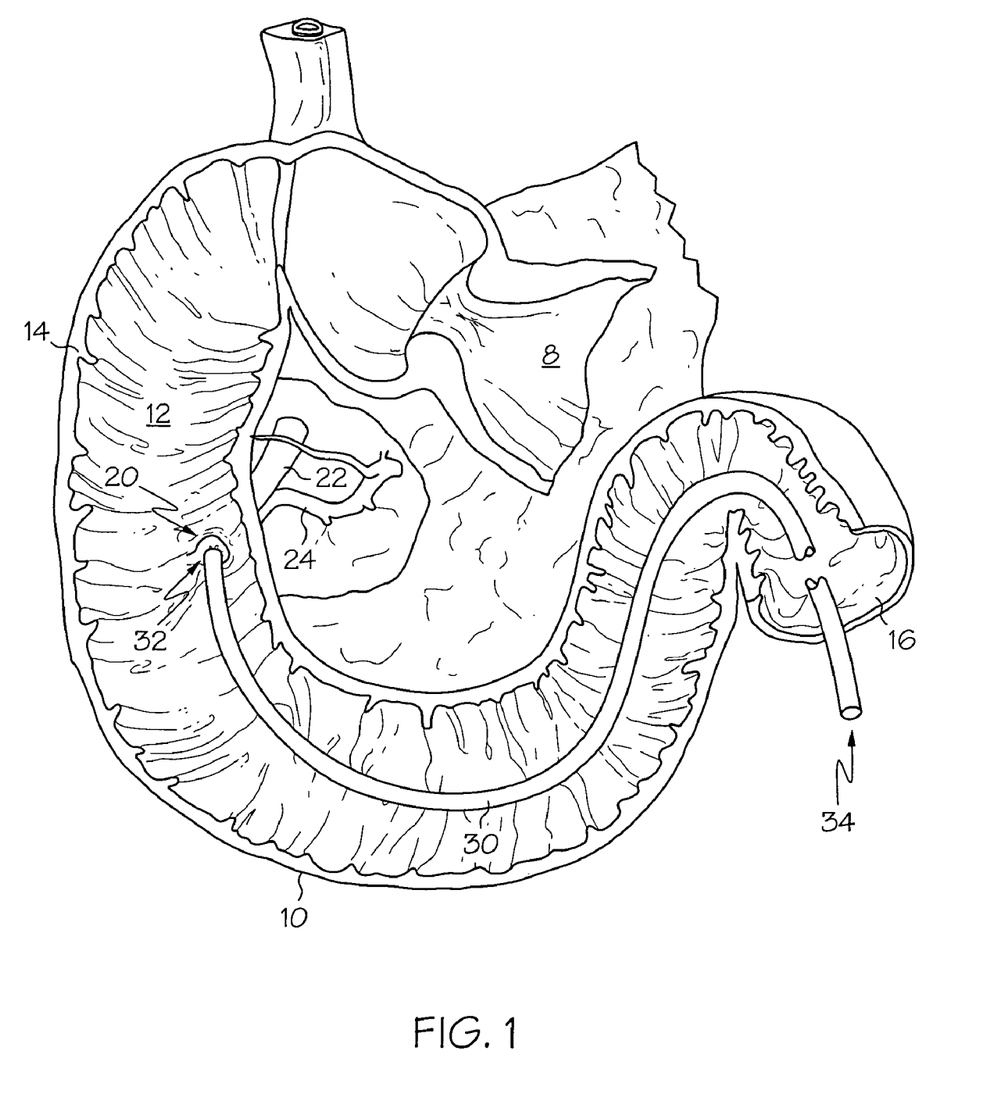
FIG. 1 depicts an example of a diversionary tube deployed in a small intestine.

FIG. 1 illustrates a cross-sectional view of the human digestive tract, including a section of the stomach (8) and the small intestine (10). As shown here the small intestine (10) includes the duodenum (12) and a section of the jejunum (16). Also shown are sections of the bile duct (22) and pancreatic duct (24), which transport bile and pancreatic secretions that discharge through the major duodenal papilla (20) into the duodenum (12). The anatomy of the bile duct (22), pancreatic duct (24) and major duodenal papilla (20) can vary. In some cases, the bile duct (22) and pancreatic duct (24) merge together into the hepatopancreatic ampulla (26), a common duct which opens through the major duodenal papilla (20) into the duodenum (12). The hepatopancreatic ampulla (26) can vary in length from one person to the next. In other cases, a person lacks a hepatopancreatic ampulla (26) in which case the bile duct (22) and pancreatic duct (24) both open directly into the duodenum (12), typically through the major duodenal papilla (20).

In one example of the invention, a diversionary tube (30) is positioned substantially within the small intestine (10) of a patient. The diversionary tube (30) comprises a proximal end (32), a distal end (34), and a tube wall having an inner surface and an outer surface whereby the inner surface defines a passage extending between the proximal end (32) and distal end (34). In the present example, the deployed state of the diversionary tube (30) comprises the proximal end (32) being positioned so as to receive digestive secretions, the distal end (34) being positioned to discharge the digestive secretions into the small intestine (10), and the passage being operative to transfer the digestive secretions from the proximal end (32) to the distal end (34). The tube wall is operative to separate the digestive secretions from food in the small intestine (10). The digestive secretions continue to flow freely but digestive contact between the bile and pancreatic secretions and food in the small intestine (10) is reduced thereby facilitating malabsorption of food nutrients and reducing caloric uptake to the patient. In addition, because the digestive secretions flow inside the diversionary tube (30), direct contact is minimized between the intestine wall and the digestive secretions, which can be irritating or caustic when not mixed with food.

The diversionary tube (30) will generally be deployed transorally using endoscopic techniques known in the art, however, the diversionary tube (30) could be deployed transanally or intrabdominally. The proximal end (32) is anchored using any one of a variety of different techniques, including without limitation using stents, sutures, staples, flanges, rings, clips, hooks, adhesives, and the like. As shown here, the proximal end (32) is anchored on or near the major duodenal papilla (20) and receives both bile and pancreatic secretions, however, it is also contemplated that the proximal end (32) could receive only one of the two digestive secretions. Before or after anchoring the proximal end (32), the distal end (34) is positioned distally in the small intestine (10). In one embodiment, the distal end (34) is deployed using the natural peristalsis and movement of food through the small intestine (10) until the diversionary tube (30) is fully extended in the small intestine (10). The degree of the malabsorption sought can be controlled by the length of the diversionary tube (30). In most cases, the distal end (34) will be positioned in the jejunum (16) or the ileum, however, it is possible the distal end (34) could be positioned in any distal location in the alimentary tract such as the duodenum (12) or the colon. The diversionary tube (30) length can be relatively long initially to maximize malabsorption, and shortened during later procedures to tailor a longer-term malabsorption rate.

Nutrient malabsorption can be used for a number of reasons. One such use is to induce weight loss as a treatment for morbid obesity. An alternative malabsorption technique is to perform a biliopancreatic diversion (BPD) procedure, which involves significant surgery to reroute the proximal portion of the small intestine. While the BPD procedure can successfully diminish the adverse effects of the co-morbidities associated with morbid obesity and significantly enhance the patient's quality of life, the treatment is highly invasive and difficult to reverse. In contrast, deployment of the diversionary tube (30) is minimally invasive and comparatively simple to reverse while providing the same or similar therapeutic benefits.

Figure 2:
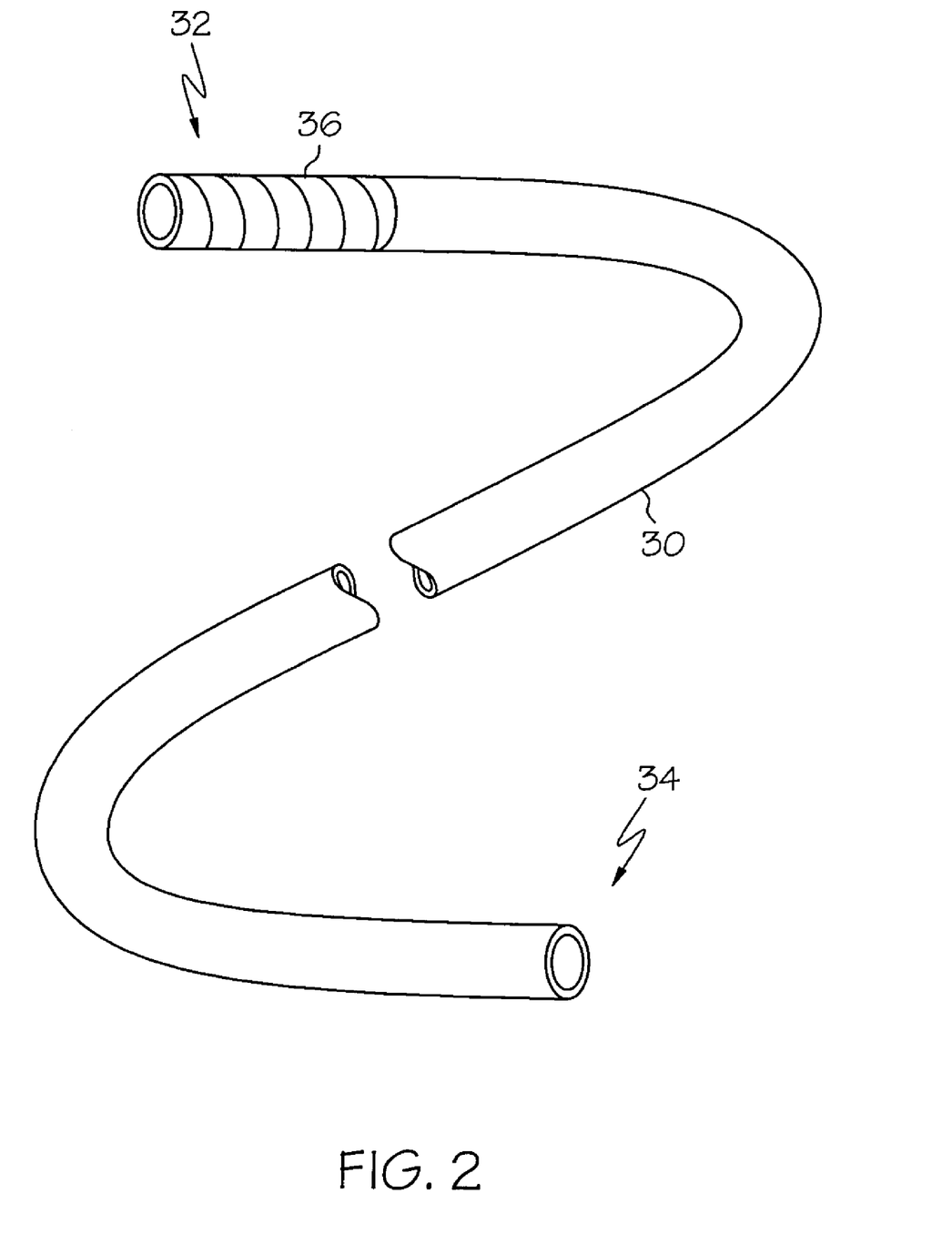
FIG. 2 depicts an example of diversionary tube with a stent.

FIG. 2 illustrates an example of a diversionary tube (30). Attached to the proximal end (32) is a stent (36) for engaging an anatomical lumen through which digestive secretions flow, such as the bile duct (22), pancreatic duct (24), or hepatopancreatic ampulla (26). The stent (36) may or may not hold sphincters open corresponding to the respective anatomical lumens. The stent (36) can take any one of a variety of configurations known in the art and dimensioned to fit in the desired anatomical lumen. In addition, the stent (36) can be lined with a sleeve of the same or different material as the diversionary tube (30). In one example, the stent (36) is an expanding nitinol stent.

The diversionary tube (30) can be made from any one of a variety of materials known in the art, including without limitation polytetrafluoroethylene or other flouropolymers, polyolefins, dacron, latex, silicone, and the like. The diversionary tube (30) may be made from a homogenous material or from a composite structure. For instance, the diversionary tube (30) could comprise an isolating layer and a separate stiffening component so as to prevent crimping or knotting. It is further contemplated that the diversionary tube (30) could be made from materials that biodegrade within a predetermined time so the diversionary tube (30) could be removed through the normal digestive processes.

The wall of the diversionary tube (30) in the present example is generally impermeable so as to minimize communication of the digestive secretions with the food until the secretions are discharged through the distal end (34). It is contemplated, however, that the diversionary tube (30) wall could be semi-permeable, for example through pores or perforations, to facilitate a gradual release of the digestive secretions into the small intestine (10). In another example, the diversionary tube (30) wall is permeable to water so moisture in the small intestine (10) would hydrate the digestive secretions in the diversionary tube (30) by virtue of an osmotic gradient and facilitate flow through the diversionary tube (30) passage. In such example, the diversionary tube (30) wall could be semi-permeable or impermeable to the digestive secretions.

Figure 3:
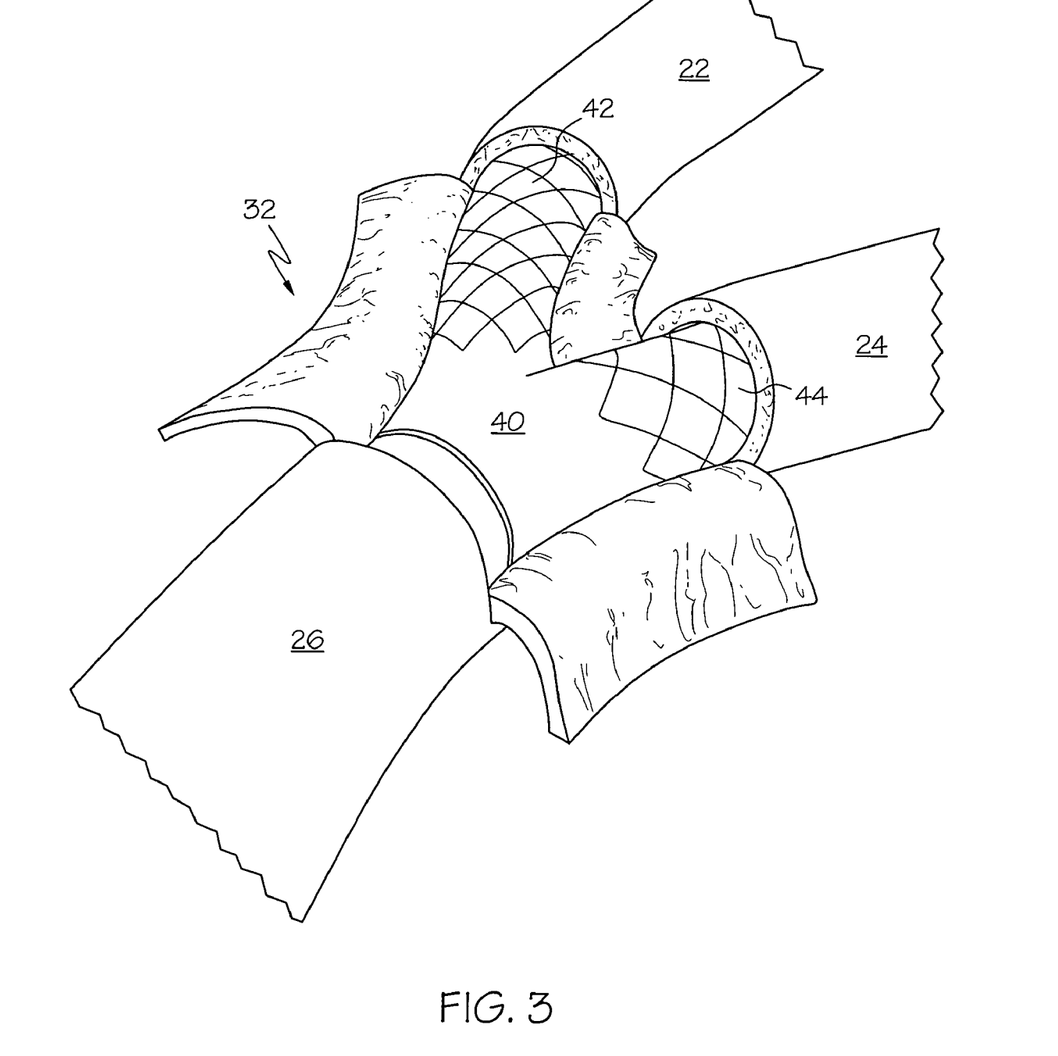
FIG. 3 depicts a dissected anatomical view with a Y-stent.

FIG. 3 illustrates an embodiment where a Y-stent (40) is connected to the proximal end (32). The Y-stent (40) includes a biliary portion (42) inserted in the bile duct (22) and a pancreatic portion (44) inserted in the pancreatic duct (24). The Y-stent (40) may or may not extend into the hepatopancreatic ampulla (26). The diversionary tube (30) extends from the Y-stent (40) in the hepatopancreatic ampulla (26) and into the small intestine (10) through the major duodenal papilla (20). Accordingly, bile flowing through the bile duct (22) and pancreatic secretions flowing through the pancreatic duct (24) will enter the proximal end (32) and flow through the diversionary tube (30).

Figure 4:
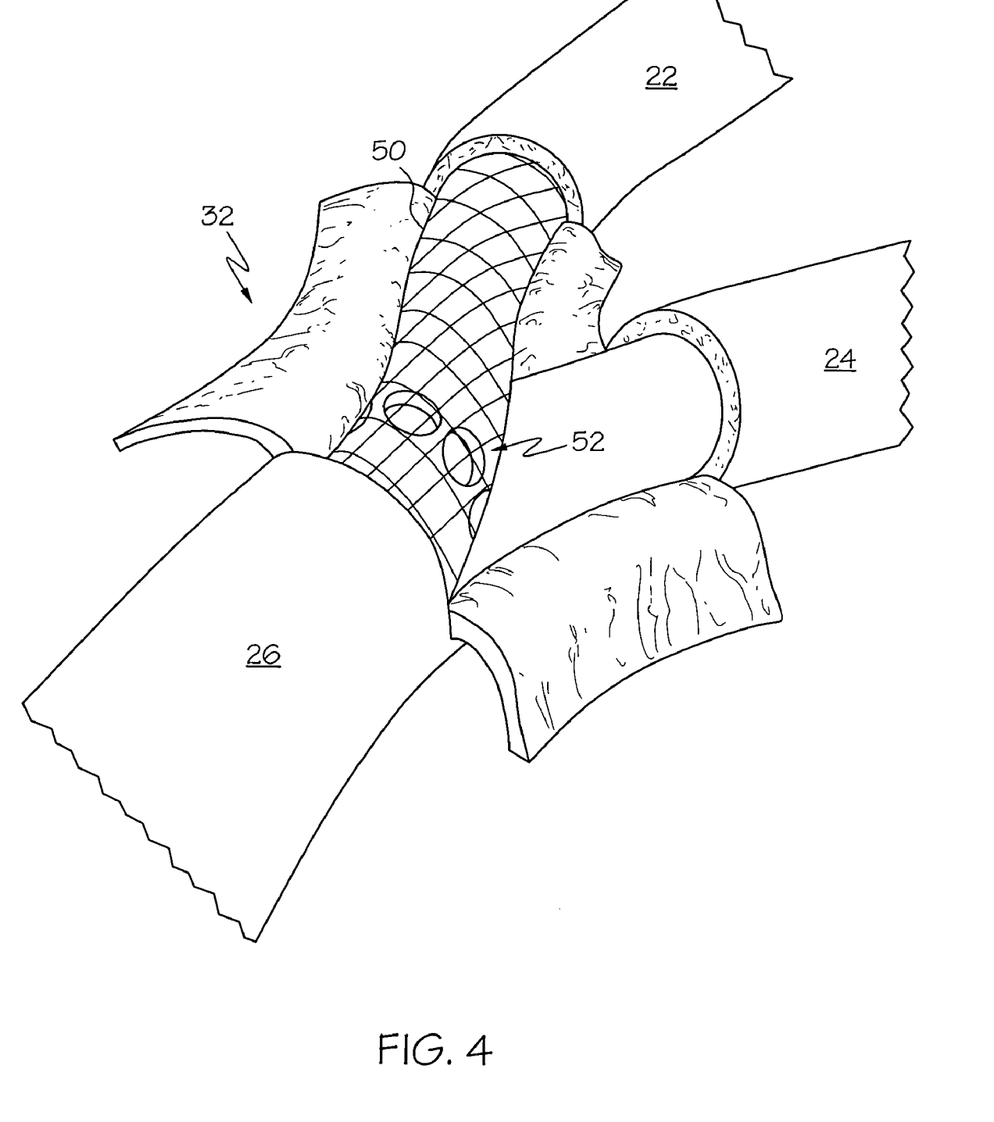
FIG. 4 depicts a dissected anatomical view with a permeable stent.

FIG. 4 illustrates an embodiment where a permeable stent (50) is connected to the proximal end (32). As shown in this example, the permeable stent (50) is partially lined and is inserted in the bile duct (22) and hepatopancreatic ampulla (26). Accordingly, bile flowing through the bile duct (22) will enter proximal end (32) of the diversionary tube (30) through the permeable stent (50). The permeable stent (50) includes a passage (52) through which pancreatic secretions flowing from the pancreatic duct (24) pass through the wall of the permeable stent (50) and enter the proximal end (32) of the diversionary tube (30). The passage (52) may take a variety of forms, including holes (as shown here), an unlined band in the permeable stent (50), or the permeable stent (50) being devoid of any lining. Alternative embodiments include the permeable stent (50) being inserted in the pancreatic duct (24) and hepatopancreatic ampulla (26), or not inserted in the hepatopancreatic ampulla (26) at all.

In another variation, the bile and pancreatic secretions are received by two diversionary tubes that maintain separation between the two digestive secretions. The diversionary tubes may be co-axial (i.e., one inside the other) or independent. One advantage of separate diversionary tubes is that the corresponding digestive secretions can be discharged at different locations along the alimentary tract by changing the length of the respective diversionary tubes. For instance, one diversionary tube could be long enough to discharge bile into the jejunum while the other diversionary tube could be long enough to discharge the pancreatic secretions into the ileum. In yet another variation, only one of the digestive secretions is diverted. For instance, pancreatic secretions can be channeled in a diversionary tube while the bile naturally discharges into the duodenum through the major duodenal papilla (or vice versa).

Figure 5:
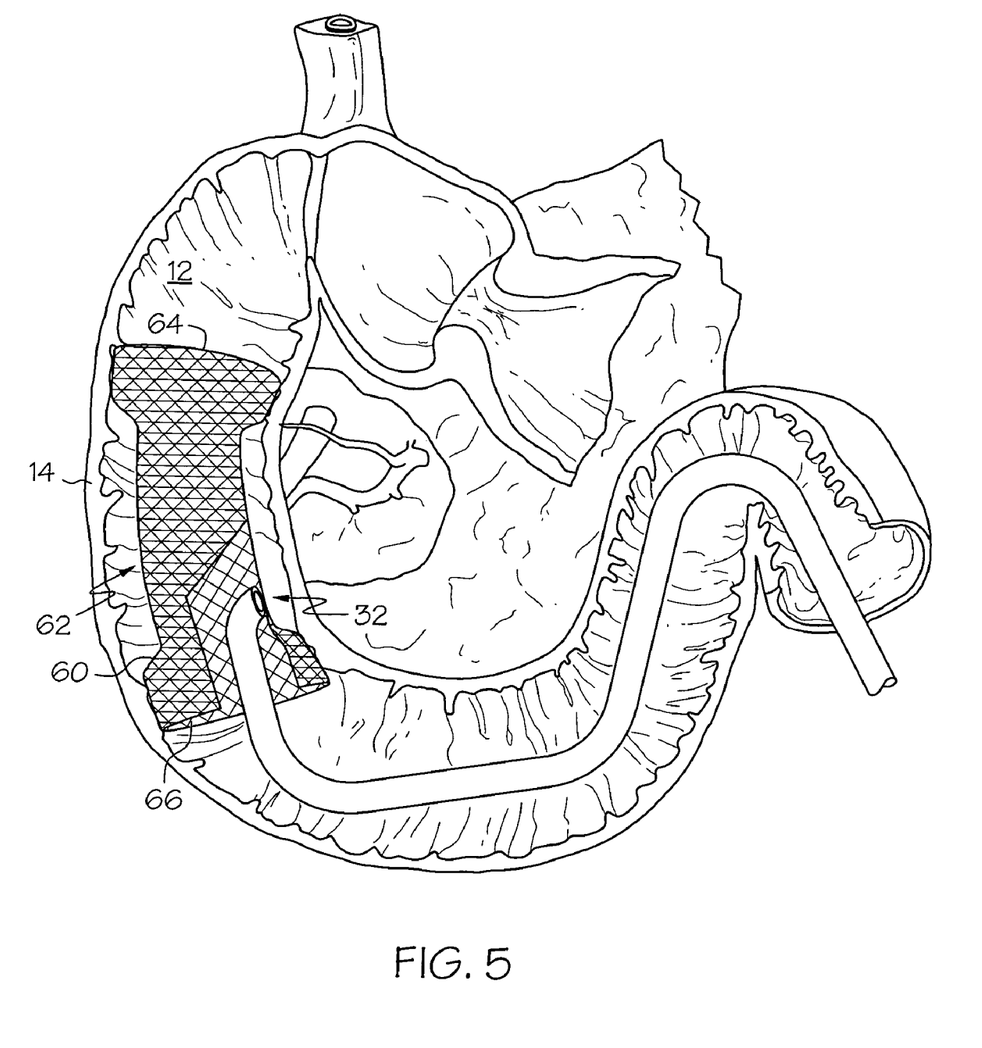
FIG. 5 depicts an example of a duodenum stent with diversionary tube.

FIG. 5 illustrates an embodiment where a duodenum stent (60) (shown here in a partial cross-section) is deployed in the anatomical lumen of the duodenum (12). In this example the duodenum stent (60) is flexible, lined, and generally hourglass-shaped. When deployed the proximal end (64) and distal end (66) substantially engage the duodenum wall (14) such that food flowing through the duodenum (12) passes through the duodenum stent (60). An annulus (62) is defined between the duodenum stent (60) and duodenum wall (14). The duodenum stent (60) is positioned in the duodenum (12) such the annulus (62) encompasses the major duodenal papilla (20). Optionally, the annulus (62) may also encompass the minor duodenal papilla (not shown). The proximal end (32) of the diversionary tube (30) extends through the distal end (66) and opens into the annulus (62), thus providing fluid communication between the annulus (62) and distal end (34) of the diversionary tube (30). Accordingly, digestive secretions will enter the annulus (62) through the major duodenal papilla (20) and/or minor duodenal papilla, enter the diversionary tube (30) through the proximal end (32), flow through the diversionary tube (30), and discharge into the small intestine (10) through the distal end (34). One advantage of the present embodiment is that it can accommodate a variety of anatomies of the bile duct (22), pancreatic duct (24) and major duodenal papilla (20). A further advantage is the device may be deployed without intervening with the pancreatic anatomy.

Having shown and described various embodiments of the present invention, further adaptations of the methods and systems described herein can be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of structure and operation shown and described in the specification and drawings.

The invention claimed is:

1. An apparatus for diverting digestive secretions discharged into a patient's intestinal tract from at least one of the duodenal papilla, the apparatus comprising:
   a) a tubular lined anchor, wherein when the anchor is deployed, a proximal end and a distal end of the anchor attach to the duodenum wall proximally and distally respectively about the duodenal papilla, for the creation of a substantially isolated chamber between an outer surface of the lined anchor and the duodenum wall, the anchor further comprising an opening extending through the lined anchor between the proximal end and distal end of the lined anchor for the passage of digestive secretions from the generally isolated chamber into the intestinal tract;
   b) a diversionary tube comprising a proximal end in fluid communication with the opening and being operative to receive digestive secretions discharged therefrom,
   a distal end which when deployed is operative to discharge the digestive secretions into the intestinal tract, and
   whereby when deployed, the apparatus is operative to transfer the digestive secretions from the isolated chamber adjacent the anchor to the distal end of the diversionary tube while exposing a substantial portion of the intestinal tract about the apparatus to contact with food.

2. The apparatus of claim 1, wherein the tube wall is substantially impermeable.

3. The apparatus of claim 1, wherein the tube wall is at least partially permeable to water.

4. The apparatus of claim 3, wherein the tube wall has an osmotic gradient.

5. The apparatus of claim 1, wherein the tube is a sufficient length so that when deployed the distal end of the tube is positioned in the jejunum.

6. The apparatus of claim 1, wherein the tube is a sufficient length so that when deployed the distal end of the tube is positioned in the ileum.

7. The apparatus of claim 1, wherein the anchor comprises a stent.

8. The apparatus of claim 7, wherein the anchor is generally hourglass-shaped.

9. The apparatus of claim 1, wherein the liner material is the same material as the tube wall.

10. The apparatus of claim 1, wherein the tube wall further comprises a stiffening component.

11. The apparatus of claim 1, wherein the tube wall is biodegradable.

12. The apparatus of claim 7, wherein the stent is expandable to attach the anchor to the duodenum.

13. The apparatus of claim 8, wherein the opening extends into a generally open passageway extending between the proximal end and the distal end.

14. The apparatus of claim 13, wherein the opening extends into a narrow waist of the passageway.

15. The apparatus of claim 1, wherein the diversionary tube has a cross section substantially smaller than the passageway to allow passage of food around the diversionary tube.

16. The apparatus of claim 1, wherein the anchor is sized to expose a substantial potion of the duodenum to contact with food.

17. The apparatus of claim 1, wherein the diversionary tube has a cross section substantially smaller than the small intestine to allow passage of food around the diversionary tube.

* * * * *